United States Patent [19]

Kaufman et al.

[11] Patent Number: 4,654,174

[45] Date of Patent: Mar. 31, 1987

[54] PREPARATION OF ALIPHATIC ANHYDRIDES AND ALKYLIDENE DICARBOXYLATES FROM DIVINYL ETHERS AND CARBOXYLIC ACIDS

[75] Inventors: James A. Kaufman, Wellesley, Mass.; Suzanne V. McKinley, Midland, Mich.

[73] Assignee: The Dow Chemical Company, Midland, Mich.

[21] Appl. No.: 382,873

[22] Filed: May 28, 1982

[51] Int. Cl.$^4$ .................. C07C 51/09; C07C 67/24; C07C 69/003; C07C 69/28; C07C 69/54

[52] U.S. Cl. .................. 260/410.6; 260/398; 260/546; 260/549; 560/224; 560/240; 560/263; 560/264; 568/397

[58] Field of Search ............... 560/224, 240, 263, 264; 260/410.6, 546, 549, 398

[56] References Cited

U.S. PATENT DOCUMENTS

| | | |
|---|---|---|
| 2,165,962 | 7/1939 | Mueller-Cunradi et al. |
| 2,296,837 | 9/1942 | Coes, Jr. .................. 560/224 |
| 2,312,193 | 2/1943 | Richter .................. 560/224 |
| 2,344,798 | 3/1944 | Brown et al. |
| 2,723,287 | 11/1955 | Copenhaver |
| 2,768,174 | 10/1956 | Paul et al. |
| 2,866,813 | 12/1958 | McTeer |
| 2,889,359 | 6/1959 | Guest et al. |
| 2,931,819 | 4/1960 | Mayne et al. .................. 260/410.9 |
| 2,978,469 | 7/1958 | Brown et al. .................. 260/410.9 |

FOREIGN PATENT DOCUMENTS

| | | | |
|---|---|---|---|
| 451810 | 10/1948 | Canada .................. 560/224 |
| 48-14615 | 2/1973 | Japan .................. 560/224 |
| 352070 | 7/1931 | United Kingdom .................. 560/240 |

OTHER PUBLICATIONS

Melick et al., "Vinyl Orthoformates and Vinyl Acetals" Recueil, 92, 775–787 (1973).

Machinskaya et al., "The reaction of Aldehydes and Ketones with Acetic Anhydride", J. Gen. Chem., USSR 23, 791-3 (1953) Eng. Trans.

Gershtein, "Transformation of Vinyl Ethers. III. Reaction of Vinyl Ethers with Organic Acids", Zhur. Obshchei Khim. (J. Gen. Chem.) 18, 1989–99 (1948).

*Primary Examiner*—Vivian Garner
*Attorney, Agent, or Firm*—N. L. Sims

[57] ABSTRACT

The invention disclosed herein is a process for preparing aliphatic anhydrides comprising contacting a divinyl ether with carboxylic acid in the presence of a catalytic amount of a strong acid. The invention is further a process for preparing alkylidene dicarboxylates, which are intermediates in the above preparation of aliphatic anhydride.

18 Claims, No Drawings

PREPARATION OF ALIPHATIC ANHYDRIDES AND ALKYLIDENE DICARBOXYLATES FROM DIVINYL ETHERS AND CARBOXYLIC ACIDS

BACKGROUND OF THE INVENTION

This invention relates to a process for preparing aliphatic anhydrides from divinyl ethers and carboxylic acid.

Divinyl ethers may be synthesized by the process disclosed by Gillis and Schimmel, *J. Org. Chem.*, 25, 2187-90 (1960).

Anhydrides are usually made by displacing chloride from an acid chloride by a carboxylate ion or by heating an acid with an acidic dehydrating agent, such as phosphorus pentoxide or acetic anhydride. These reactions require either high temperatures or generate inorganic waste products.

SUMMARY OF THE INVENTION

The invention is a process for preparing aliphatic anhydrides comprising contacting a divinyl ether with a carboxylic acid in the presence of a catalytic amount of a strong acid. The invention is further a process for preparing alkylidene dicarboxylates, which are intermediates in the above preparation of aliphatic anhydrides.

DETAILED DESCRIPTION OF THE INVENTION

The divinyl ethers used in this invention are represented by the formula

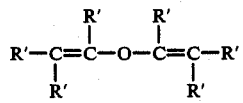

wherein R' is separately in each occurrence a substituted or unsubstituted $C_{1-10}$ aliphatic group or a hydrogen atom. Preferably, the starting divinyl ether is symmetrical. Most preferably, the starting ether is diisopropenyl ether, which is represented by the formula $$CH_2=\overset{CH_3}{\underset{|}{C}}-O-\overset{CH_3}{\underset{|}{C}}=CH_2.$$

In the invented process, these divinyl ethers are reacted with carboxylic acids. Preferably, the carboxylic acids are substituted and unsubstituted aliphatic carboxylic acids. More preferably, the carboxylic acid is 1 to 10 carbon alkenyl or alkyl carboxylic acids. Most preferably, the carboxylic acid is acetic acid, propionic acid or acrylic acid.

The reactants should be combined in about a 2 to 1 ratio of the carboxylic acid to the dialkenyl ether.

In this process carboxylic acid reacts with divinyl ether to form an intermediate which is an alkylidene dicarboxylate, formula II below, and a carbonyl compound, formula III below. This reaction can be represented by the following equation, A:

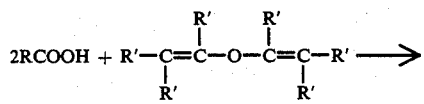

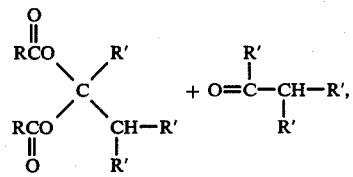

wherein R' is separately in each occurrence a 1 to 10 carbon aliphatic group or a hydrogen atom; and R is a substituted or unsubstituted aliphatic group. More preferably, R is $C_{1-10}$ alkenyl or $C_{1-10}$ alkyl.

The alkylidene dicarboxylate (II) is a fairly stable compound which is an intermediate in the production of the anhydride. The compound decomposes with heating to the anhydride (I) and the carbonyl compound (III). This can be represented by the following equation, B:

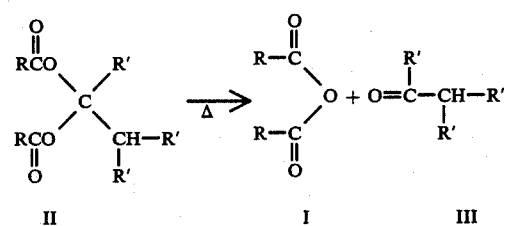

R and R' are defined above. Where the most preferred divinyl ether, diisopropenyl ether is used, the reaction can be described by the following equations:

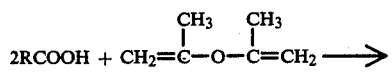

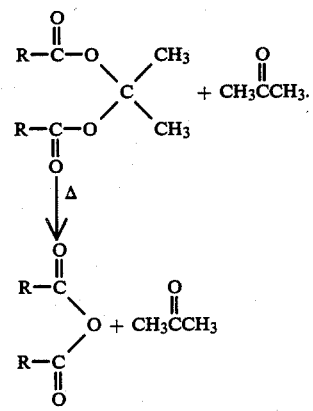

In this embodiment of the invention, the carbonyl compound (III) is acetone.

The reaction is catalyzed by a strong acid. Preferable strong acids are those with a $pK_a$ of less than 2.0. More preferably, the acids are oxalic acid and trifluoroacetic acid. The catalyst is preferably used in mole ratios of catalyst to divinyl ether of between about 0.5 to 1.0 and 0.001 to 1.0 and more preferably between about 0.1 to 1.0 and 0.01 to 1.0. Other strong acids which may be used include sulfuric acid, hydrochloric acid and nitric acid.

Where the carboxylic acid is a liquid, no solvent is necessary, although a solvent may be used. Suitable solvents include inert organic solvents, preferably chlorinated aliphatic compounds, most preferably those represented by the formula $CCl_xY_{4-x}$, wherein x is an integer from 1 to 4 inclusive and Y is hydrogen or deuterium. To get the desired product of the anhydride, the most preferable solvents are those represented by the formula $CCl_3Y$. It has been discovered that the use of $CDCl_3$ and $CHCl_3$ as solvents speeds up the reaction and aids the decomposition of the alkylidene dicarboxylate to the anhydride.

Some alkylidene dicarboxylates are more stable than others, and elevated temperatures are required for some of the alkylidene dicarboxylates to decompose to give the anhydride product. Elevated temperatures mean herein above 60° C., preferably between 120° C. and 500° C. Between 25° C. and 60° C., the alkylidene dicarboxylate is the predominant product of this reaction. Between 60° C. and 120° C. both the alkylidene dicarboxylate and the aliphatic anhydride are produced in substantial amounts.

Where propionic anhydride is the desired product, the reaction temperature should be between about 30° C. and 200° C. It is preferable to run the reaction between about 80° C. and 180° C., and most preferable to run it at a temperature between about 120° C. and 150° C. In the most preferred range, almost all of the alkylidene dicarboxylate decomposes.

When acrylic acid is the starting carboxylic acid, the alkylidene dicarboxylate formed is very stable. In order for the alkylidene dicarboxylate of acrylic acid to decompose to the anhydride, the alkylidene dicarboxylate of acrylic acid is preferably exposed to temperatures, up to about 400° C.

When the alkylidene dicarboxylate is subjected to gas pyrolysis, it decomposes to the anhydride and the carbonyl compound. The pyrolysis step can be run between about 250° C. and 400° C. Thus, the process for preparing the anhydride disclosed herein can additionally include a gas pyrolysis step wherein a particularly stable alkylidene dicarboxylate is decomposed to give the anhydride. Where acrylic acid is the starting carboxylic acid, the alkylidene dicarboxylate produced decomposes to acrylic anhydride and the carbonyl compound when subjected to gas pyrolysis.

When acrylic anhydride is the desired product, $CDCl_3$ or $CHCl_3$ are the preferred solvents as acrylic anhydride is a significant portion of the product when those solvents are used.

This process can be run at autogeneous pressure. The process may be run in an inert gas atmosphere, such as $N_2$.

Specific Embodiments

The practice of the instant invention is further illustrated by the following examples. These embodiments and examples are not intended to limit the scope of the instantly claimed invention.

EXAMPLE 1

Reaction of Diisopropenyl Ether with Acetic Acid

Diisopropenyl ether (4.9 g, 0.05 mole, 97 percent pure) and acetic acid (6.0 g, 0.10 mole) were combined in a round-bottom flask outfitted with a condenser, thermometer and $N_2$ blanket, and refluxed (60° C.) for 2 hours. Gas chromatographic analysis showed the reaction had not gone to completion based on acetic acid remaining. Two drops of trifluoroacetic acid were added and the reaction went to completion with the formation of two major products, acetic anhydride and 2,2,-propane diacetate (alkylidene dicarboxylate). The volatiles were removed on a rotary evaporator and the two major products constituted 95 percent of the gas chromatograph area in a ratio of 1:1.4, acetic anhydride to 2,2,-propane diacetate.

This example demonstrates the catalytic effect of the strong acid and the products which result from the reaction.

EXAMPLE 2

Reaction of Diisopropenyl Ether with Propionic Acid

Propionic acid (3.9 ml, 0.052 mole) was added dropwise to stirring diisopropenyl ether (2.55 g, 0.026 mole) in a 25-ml, 3-neck round-bottom flask equipped with condenser, dropping funnel, thermometer and $N_2$ blanket. Oxalic acid (50 mg) was added causing an immediate rise in temperature from 25° C. to 38° C. The reactants were allowed to react at 25° C. for 68 hours. Thereafter, the temperature of the reaction mixture was raised to 60° C. and kept there for 72 hours. This reaction was followed by gas chromatography as samples of the mixture were taken periodically.

The reaction did not reach completion after 72 hours at 60° C. Heating at 60° C. enhanced formation of both the propionic anhydride and the 2,2-propane dipropionate (the alkylidene dicarboxylate). Table I shows the gas chromatographic data relative to the amounts of alkylidene dicarboxylate and aliphatic anhydride produced.

TABLE I

Gas Chromatographic Results for the Reaction of Diisopropenyl Ether with Propionic Acid at Moderate Temperature (60° C.)

| | | Area % | |
|---|---|---|---|
| Time (hr) | Temp (°C.) | Propionic Anhydride | Alkylidene Dicarboxylate (2,2-propane-dipropionate) |
| 0[a] | 25 | 0.33 | 0.63 |
| 0[b] | 25 | 1.54 | 1.89 |
| 1 | 25 | 2.84 | 4.29 |
| 68 | 25 | 9.73 | 26.26 |
| 1.5[c] | 60 | 13.45 | 32.74 |
| 18 | 60 | 18.32 | 39.84 |
| 24 | 60 | 20.14 | 42.65 |
| 42 | 60 | 20.08 | 52.78 |
| 72 | 60 | 15.10 | 66.06 |

[a]Without oxalic acid catalyst.
[b]With catalyst.
[c]At the change in temperature, time is recorded as starting from 0.

EXAMPLE 3

Reaction of Propionic Acid and Diisopropenyl Ether at Elevated Temperatures

Diisopropenyl ether (7.42 g, 0.076 mole) and oxalic acid (0.056 g, 0.06 mmole) were combined in a reaction vessel like that used in Example 2. Propionic acid (11.2 ml, 0.15 mole) was added dropwise with stirring and the reaction mixture was held at 35° C. with an ice bath. Upon completion of the addition, the reaction mixture was heated to 60° C. for 23 hours. Thereafter the temperature was raised to 100° C. for 23 hours and then 140° C. for 5 hours, after which gas chromatography and nuclear magnetic resonance indicated the reaction was complete.

The reaction was followed by gas chromatography and the data relative to the amounts of alkylidene dicarboxylate and aliphatic anhydride produced are compiled in Table II.

TABLE II

Gas Chromatographic Results for
the Reaction of Diisopropenyl Ether
with Propionic Acid at
Elevated Temperature (60° C.–140° C.)

| | | Area % | |
|---|---|---|---|
| Time[a] (hr) | Temp (°C.) | Propionic Anhydride | Alkylidene Dicarboxylate (2,2-propane-dipropionate) |
| 0 | 25 | 1.20 | 1.92 |
| 0 | 60 | 2.11 | 4.43 |
| 0.17 | 60 | 3.38 | 10.13 |
| 0.33 | 60 | 4.54 | 12.32 |
| 0.5 | 60 | 5.40 | 14.78 |
| 0.67 | 60 | 6.26 | 17.14 |
| 1.0 | 60 | 7.40 | 19.79 |
| 1.5 | 60 | 8.22 | 21.58 |
| 2.5 | 60 | 9.75 | 24.97 |
| 3.5 | 60 | 10.55 | 26.54 |
| 17.5 | 60 | 15.92 | 39.35 |
| 19.5 | 60 | 16.29 | 40.77 |
| 25.5 | 60 | 16.96 | 43.58 |
| 28.0 | 60 | 15.78 | 44.42 |
| 1.0 | 100 | 16.50 | 45.42 |
| 2.0 | 100 | 16.65 | 45.24 |
| 4.0 | 100 | 17.54 | 45.13 |
| 6.5 | 100 | 18.56 | 44.89 |
| 20.0 | 100 | 25.42 | 35.61 |
| 23.0 | 100 | 27.35 | 35.44 |
| 1.0 | 140 | 39.14 | 17.55 |
| 2.0 | 140 | 45.04 | 6.25 |
| 4.0 | 140 | 53.52 | 1.39 |
| 5.0 | 140 | 57.23 | 0.87 |

[a] At each increment in temperature, time is recorded as starting from 0.

These data show that the 2,2-propane dipropionate and propionic anhydride concentrations increase at 60° C. with the former forming more rapidly and reaching its maximum concentration after 28 hours. At 100° C. the 2,2,-propane dipropionate reaches its maximum concentration after about 1 hour, thereafter it starts to decompose to propionic anhydride.

EXAMPLE 4

Preparation of Propionic Anhydride from Propionic Acid and Diisopropenyl Ether

A solution of oxalic acid (0.23 g, 0.003 mole) in propionic acid (29.0 ml, 0.39 mole) was added dropwise with stirring to diisopropenyl ether (18.38 g, 0.188 mole) at 0° C. to 10° C. in a 100-ml reaction flask equipped as described in the above examples. The flask was placed in a preheated (65° C.) oil bath to begin the reaction. The temperature was gradually increased to 120° C. and the reaction was followed by gas chromatography. Upon completion of the reaction, the anhydride concentration, as measured by gas chromatography, was 97 percent and no 2,2-propane dipropionate was present in the product. The data relative to the amounts of alkylidene dicarboxylate and aliphatic anhydride generated by this test are compiled in Table III.

TABLE III

Gas Chromatographic Results for
the Reaction of Diisopropenyl Ether
with Propionic Acid

| | | Area % | |
|---|---|---|---|
| Time (hr) | Temp (°C.) | Propionic Anhydride | Alkylidene Dicarboxylate (2,2-propane-dipropionate) |
| 0 | 25 | 0.70 | 0.82 |
| 0 | 60 | 1.73 | 3.15 |
| 17 | 60 | 14.71 | 32.58 |
| 5 | 90 | 20.56 | 43.15 |
| 5 | 110 | 21.22 | 38.85 |
| 7 | 110 | 26.74 | 44.32 |
| 17 | 120 | 63.80 | — |

EXAMPLE 5

Reaction of Acrylic Acid and Diisopropenyl Ether

Diisopropenyl ether (105.9 g, 1.03 moles, 95.5 percent pure) was placed in a 500-ml, 3-neck flask fitted with a magnetic stirrer, thermometer, condenser and dropping funnel with a pressure equalizing side-arm. p-Methoxyphenol (0.025 g, 0.002 mole) was added as an inhibitor and oxalic acid (0.96 g, 0.01 mole) was added as a catalyst. Acrylic acid (165.7 g, 2.3 moles) containing 200 ppm p-methoxyphenol was added slowly to the reaction vessel by the dropping funnel. An ice bath was used to keep the reaction mixture temperature between 22° C. and 25° C. during the addition. The reaction was followed by periodically removing samples and analyzing them by gas chromatography. After 2 days, the reaction mixture had a constant composition. After distillation, 101.0 g of 95 percent by gas-liquid chromatography area of 2,2-propane diacrylate (a 51 percent isolated yield) were recovered. Only traces of acrylic anhydride were observed throughout the reaction. The p-methoxyphenol was added to inhibit polymerization. Later testing determined its use was unnecessary.

EXAMPLE 6

Pyrolysis of 2,2-Propane Diacrylate

Microliter quantities of 2,2-propane diacrylate were pyrolyzed in the injection block of a Hewlett-Packard 5712A gas chromatograph at temperatures ranging from 250° C. to 400° C. Gas chromatographic analysis of the pyrolysates showed that the concentration of the acrylic anhydride in the reaction mixture had increased significantly.

EXAMPLE 7

Effect of CDCl$_3$ on Reaction of Acrylic Acid with Diisopropenyl Ether

Acrylic acid (1.47 g, 0.02 mole), diisopropenyl ether (0.99 g, 0.01 mole) and oxalic acid (0.008 g, $8.9 \times 10^{-5}$ moles) were mixed in a nitrogen-filled 10-ml volumetric flask. A 30-$\mu$l aliquot of this mixture was transferred to a nuclear magnetic resonance tube, mixed with CDCl$_3$ (0.5 ml), methylene chloride (10 $\mu$) and tetramethylsilane. After 24.5 hours, the sample in the nuclear magnetic resonance tube showed that the reaction was almost complete as the acid was nearly consumed. The amount of acrylic anhydride produced was 1.5:1 to that of the 2,2-propane diacrylate. Conversely the mixture in the original volumetric flask had a much lower conversion of reactants to products and almost no anhydride.

After 14 days, the amount of acrylic anhydride in the nuclear magnetic resonance tube increased while that in the volumetric flask did not. The ratio of acrylic anhydride to 2,2-propane diacrylate was 3.3:1.

The CDCl₃ has some solvent effect on the formation of an anhydride over the alkylidene dicarboxylate. The product mix is also affected by the length of time of the reaction in that yield of anhydride increases with time.

EXAMPLE 8

Effect of CDCl₃ on the Reaction of Propanoic Acid with Diisopropenyl Ether

As a point of comparison for following the formation of propionic anhydride distillative isolation, nuclear magnetic resonance and gas chromatographic analysis were performed on the initial reaction mixture of Example 4. The nuclear magnetic resonance spectrum in CDCl₃ showed an absence of diisopropenyl ether, low levels of the 2,2-propane dipropionate and high levels of propionic anhydride and acetone. During the nuclear magnetic resonance analysis, the sample had undergone a color change from colorless to dark yellow. Gas chromatographic analysis on the initial reaction mixture and on the sample used for nuclear magnetic resonance gave the following reactant/product distribution:

TABLE IV

| Area % | Anhydride | Alkylidene Dicarboxylate |
|---|---|---|
| Initial (neat) | 0.70 | 0.80 |
| After nmr (CDCl₃) | 1.48 | 0.05 |

There is a solvent effect with CDCl₃ which causes decomposition of the alkylidene dicarboxylate to the anhydride and acetone.

What is claimed is:

1. A process for preparing aliphatic anhydrides comprising contacting a divinyl ether with a carboxylic acid in the presence of a catalytic amount of a strong acid to prepare a reaction product comprising an alkylidene dicarboxylate and exposing the reaction mixture to reaction conditions such that an aliphatic anhydride is prepared.

2. The process of claim 1 wherein the reaction is run in an inert organic solvent.

3. The process of claim 2 wherein the solvent is a chlorinated aliphatic compound.

4. The process of claim 3 wherein the solvent is selected from the group consisting of solvents represented by the formula CCl$_x$Y$_{4-x}$ wherein x can be an integer selected from the group 1, 2, 3 and 4, and Y is hydrogen or deuterium.

5. The process of claim 4 wherein the solvent is chosen from the group consisting of CCl₃Y.

6. The process of claim 1 wherein the divinyl ether is represented by the formula:

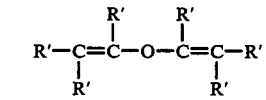

wherein R' is separately in each occurrence a substituted or unsubstituted C$_{1-10}$ aliphatic group or a hydrogen.

7. The process of claim 6 wherein the divinyl ether is symmetrical.

8. The process of claim 7 wherein the divinyl ether is diisopropenyl ether.

9. The process of claim 8 wherein the carboxylic acid is selected from the group consisting of acetic, propionic and acrylic acids.

10. The process of claim 6 wherein the carboxylic acid is selected from the group consisting of substituted and unsubstituted aliphatic carboxylic acids.

11. The process of claim 10 wherein the carboxylic acid is selected from the group consisting of C$_{1-10}$ alkenyl and alkyl carboxylic acids.

12. The process of claim 11 wherein the carboxylic acid is selected from the group consisting of acetic, propionic and acrylic acids.

13. The process of claim 6 wherein the catalyst is a strong acid with a pK$_a$ of less than 2.0.

14. The process of claim 13 wherein the catalyst is selected from the group consisting of trifluoroacetic and oxalic acids.

15. A process for preparing an alkylidene dicarboxylate represented by the formula

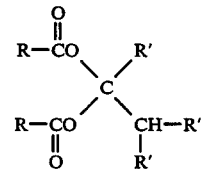

wherein R is C$_{1-10}$ alkenyl or alkyl, and R' is separately in each occurrence substituted or unsubstituted C$_{1-10}$ aliphatic or hydrogen; comprising contacting a divinyl ether with a carboxylic acid in the presence of a catalytic amount of a strong acid under conditions such that an alkylidene dicarboxylate is prepared.

16. The process of claim 15 wherein the reaction temperature is between about 25° C. and 60° C.

17. The process of claim 16 wherein the divinyl ether is represented by the formula:

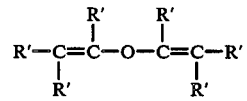

wherein R' is separately in each occurrence a substituted or unsubstituted C$_{1-10}$ aliphatic group or a hydrogen.

18. The process of claim 17 wherein the divinyl ether is diisopropenyl ether.

* * * * *